Figure 1:
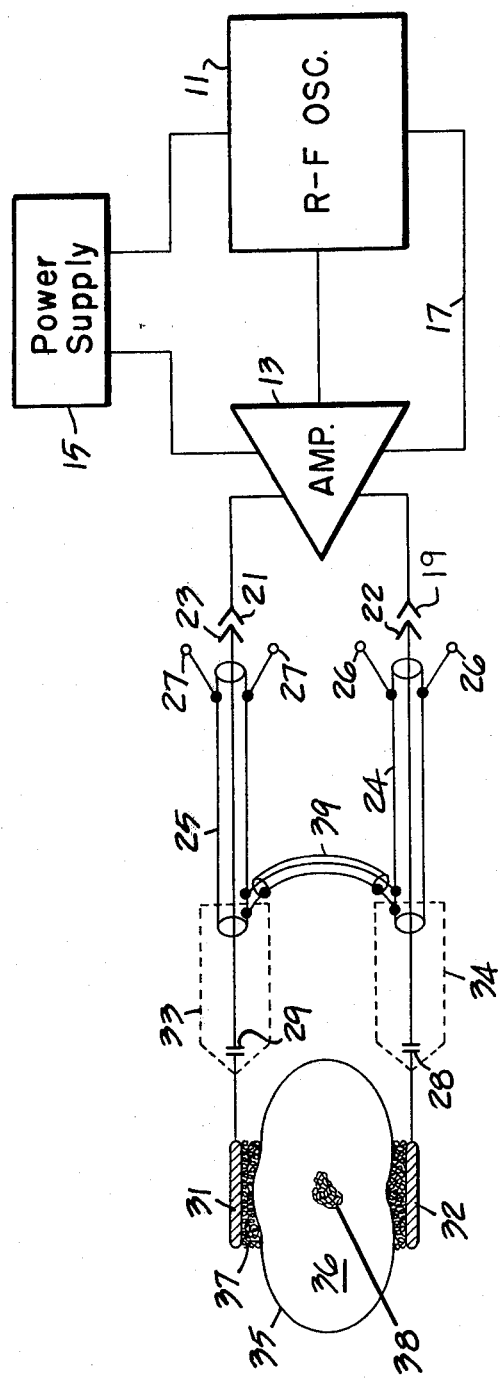

United States Patent [19]

Whalley

[11] 4,237,898

[45] Dec. 9, 1980

[54] APPARATUS FOR HEATING TISSUE AND EMPLOYING PROTECTION AGAINST TRANSIENTS

[75] Inventor: Wilfrid B. Whalley, Palo Alto, Calif.

[73] Assignee: Critical Systems, Inc., Palo Alto, Calif.

[21] Appl. No.: 890,693

[22] Filed: Mar. 27, 1978

Related U.S. Application Data

[63] Continuation-in-part of Ser. No. 705,524, Jul. 20, 1976, Pat. No. 4,121,592, which is a continuation-in-part of Ser. No. 643,515, Dec. 22, 1975, abandoned, which is a continuation-in-part of Ser. No. 601,257, Aug. 4, 1975, abandoned.

[51] Int. Cl.³ .............................................. A61N 1/32
[52] U.S. Cl. ..................................... 128/422; 128/804
[58] Field of Search ............... 128/404, 413, 422, 399, 128/421, 423 R, 785, 784, 798, 802, 804

[56] References Cited

U.S. PATENT DOCUMENTS

| | | | |
|---|---|---|---|
| 1,585,795 | 5/1926 | Speter | 128/783 |
| 1,889,609 | 11/1932 | Mutscheller | 128/422 |
| 3,898,991 | 8/1975 | Ikuno et al. | 128/422 X |
| 3,991,770 | 11/1976 | LeVeen | 128/413 |
| 4,016,886 | 4/1977 | Doss et al. | 128/422 |
| 4,032,860 | 6/1977 | LeVeen | 128/422 X |
| 4,140,130 | 2/1979 | Storm | 128/404 |

OTHER PUBLICATIONS

Gerner et al., "The Potential . . . Therapy", Radiology, 116: 433–439, Aug. 1975.
Geyser, "Diathermia . . . of Cancer", Fischer's Magazine, 1925.
Dickson et al., "Tumor Eradication . . . RF Heating", Cancer Research, 37, 2162–2169, Jul. 1977.
Lehmann et al., "Evaluation of a Microwave Contact Applicator", Archives . . . Med. & Rehabilitation, Mar. 1970, pp. 143–146.
Dickens et al., "The Action of Short Radio Waves on Tissue", Am. J. Cancer, vol. 30, No. 2, Jun. 1937, pp. 341–354.

*Primary Examiner*—Lee S. Cohen
*Attorney, Agent, or Firm*—Fitch, Even, Tabin, Flannery & Welsh

[57] ABSTRACT

Apparatus is described for heating tissue and which is particularly useful for treating tumors in humans and animals. A radio frequency a-c electric current is caused to flow between two electrodes or one electrode and ground directly through both the tumor and the surrounding tissue. The current is controlled to cause heating of the tumor and the surrounding tissue such that the tumor heats to a level sufficient to cause necrosis without substantial damage to the surrounding tissue.

3 Claims, 2 Drawing Figures

APPARATUS FOR HEATING TISSUE AND EMPLOYING PROTECTION AGAINST TRANSIENTS

This application is a continuation-in-part of application Ser. No. 705,524 filed July 20, 1976 and now U.S. Pat. No. 4,121,592, which was a continuation-in-part of application Ser. No. 643,515 filed Dec. 22, 1975, now abandoned, which was a continuation-in-part of application Ser. No. 601,257, filed Aug. 4, 1975, now abandoned.

This invention relates generally to the treatment of tissue. More particularly, the invention relates to apparatus for heating tumors in humans and animals to a higher temperture than the surrounding tissue.

One of the known characteristics of certain types of tumors is that the blood circulation rate therein is significantly less than that in normal or healthy tissue. (See Encyclopedia Britannica p. 769—"Cancer"). For example, certain types of tumors have a blood circulation rate which is at least as low as one-half that of normal surrounding healthy tissue. This fact is considered to be the cause of a contributory factor in the selective heat sensitivity of many types of malignant tumors.

The treatment of tumors by selective heating has been reported in the literature. (See Surgery, Gynecology and Obstetrics, Volume 140, No. 3, March 1975, *Results of Hyperthermic Perfusion for Melanoma of the Extremities*, Stehlin, Jr., Giovanella, Ipolyi, Muenz, and Anderson.). Techniques for selective heating have included hyperthermic perfusion, diathermy, and the induction of fever.

For various reasons, however, success in the treatment of tumors and in particular malignant tumors has been limited. For example, in the case of hyperthermic perfusion, some undesirable damage to healthy tissue has often resulted and the technique is only suitable for the treatment of tumors in limbs. Although a form of diathermy has been used successfully to treat tumors near the skin surface, specifically the use of a probe or stylus inside the rectum to produce a small area of electrically induced heating in the treatment of rectal tumors, tumors any substantial distance below the surface of the skin have typically been untreatable. Finally, although fever has caused remission in some cases, prolonged induction of fever may have considerable undesirable side effects.

Experiments conducted at the Royal Victoria Infirmary, Newcastle-Upon-Tyne, England, during the late 1930's have been reported in the American Journal of Cancer, Vol. 28, November, 1936, pp. 603–620; Vol. 30, June, 1937, pp. 341–354; and Vol. 38, 1940, pp. 533–550. These experiments succeeded in destroying tumors in rats and mice through the use of radio frequency electric fields. Treatment, however, was limited for the most part to relatively small volumes of tissue, and success was generally limited to surface tumors. In many cases the skin was damaged as well as the tumor. Moreover, very high field densities were employed in the aforementioned experiments resulting in little if any selective heating between the tumor and the surrounding tissue. Finally, the frequencies used in the experiments and the type of apparatus employed resulted in poor coupling of the power of the apparatus into the tissue being heated and poor control over power levels.

The basic elements described above are disclosed by the prior art. Thus, Wappler U.S. Pat. No. 1,480,353, Jan. 8, 1924, shows the use of a pair of padded capacitive plates attached to handles and used to apply high frequency currents to human tissue for medical or therapeutic purposes. Carpenter et al, "Production of Fever in Man by Short Wave Radio Waves", Science, May 2, 1930, LXXI, 450-2, discuss the production of artificial fever in man by short radio waves to whole body temperature of 104° F. to 105° F. for therapeutic purposes. A frequency of $10^4$ MHz was used with capacitive plates $28 \times 18$ inches covered by rubber insulation. The vacuum tube oscillator had an output of 500 watts at 3,000 volts. Schereschewski, J. W., Radiology 20:246, 1933, suggested the use of high frequency condenser fields to raise the temperature of deep-seated organs to a considerable degree without, at the same time, overheating the subcutaneous tissue.

Although the production of a high frequency electric field is relatively simple from an engineering point of view, the above reports suggest considerable lack of sophistication in the apparatus used. The mere connection of a pair of capacitive plates to the combination of an oscillator and amplifier does not provide the degree of control over heating rates and temperatures needed for a truly effective tumor treatment.

It is an object of the present invention to provide an improved apparatus for the treatment of tumors.

Another object of the invention is to provide an improved apparatus for heating tumors without adverse effects to surrounding tissue.

A further object of the invention is to provide apparatus for heating tumors to a higher temperature than the surrounding tissue.

Figure 2:
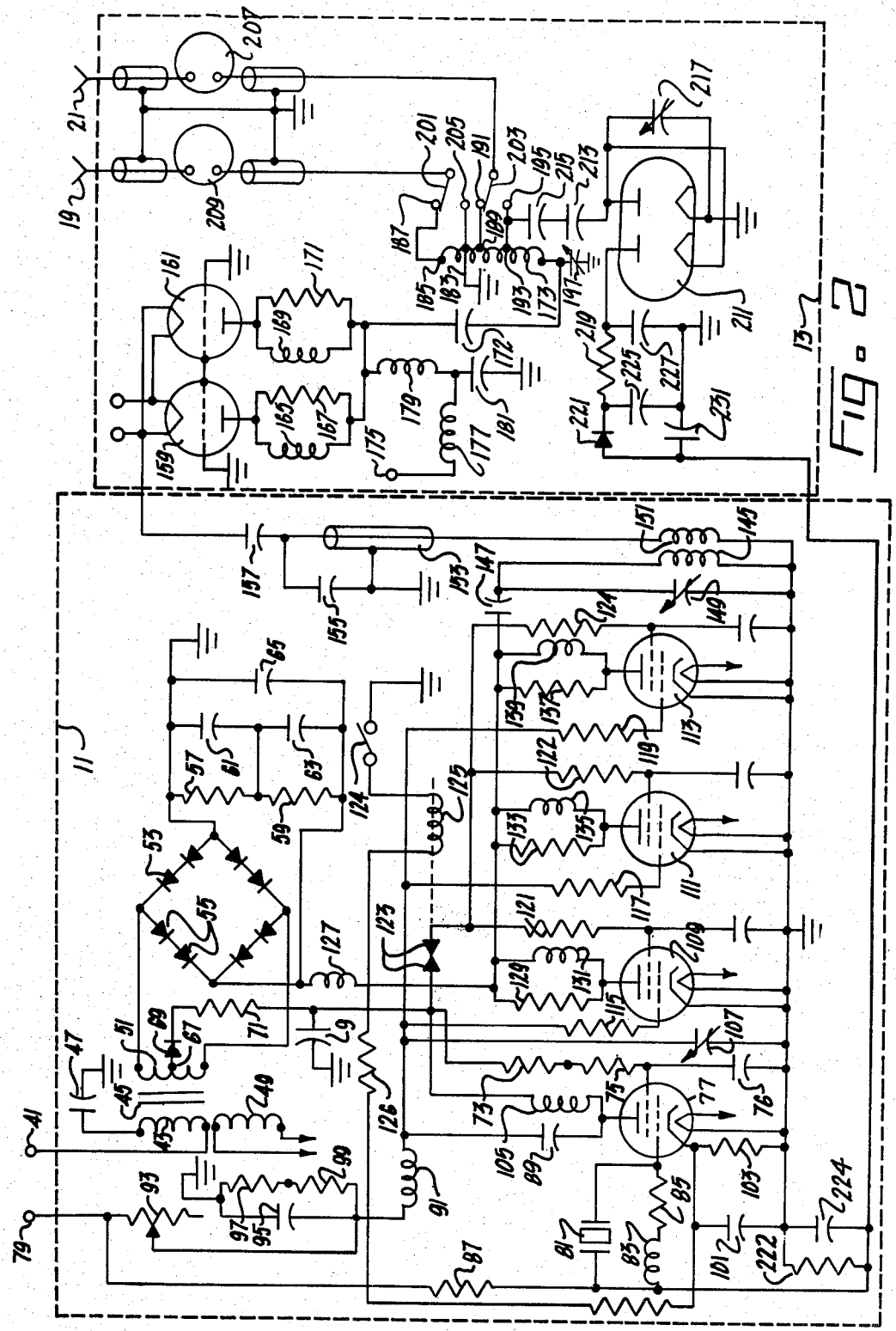

Other objects of the invention will become apparent to those skilled in the art from the following description, taken in connection with the accompanying drawings wherein:

FIG. 1 is a schematic block diagram of apparatus constructed in accordance with the invention; and FIG. 2 is a circuit diagram illustrating one form of a portion of the apparatus of the invention.

Very generally, the apparatus of the invention comprises radio frequency oscillator means and amplifier means coupled to the output of the radio frequency oscillator means for producing an amplified radio frequency output signal. Electrode means are coupled to the amplifier means and include a pair of uninsulated conductive electrodes having a configuration adapted to pass an electric current directly into the tissue to which they are attached by passing current through both the tumor and the surrounding tissue. Means are provided for controlling the power of the amplifier means to avoid heating the surrounding tissue beyond a preselected temperature level while allowing the tumor to heat beyond the preselected temperature level.

The higher sensitivity of malignant tumors to heat has been taken advantage of in a number of techniques as previously mentioned. One such technique is the use of so-called diathermy in which magnetic fields produced by suitable coils of the type used for physical therapy have been used to attempt to heat malignant tumors. The results of such attempts, however, have produced very limited, if any, success. Attempts to heat tumors typically resulted in damage to the skin, without successful results in destroying the tumor.

The present invention results from a recognition that diathermy techniques for the treatment of malignant tumors did not succeed because of electrical current skin effects inherent with live tissue in electromagnetic fields, and also the very limited volume of the effective electromagnetic field (that is an effective field only in close proximity to the coil itself). More particularly, any tissue which has a resistivity of approximately 50 ohms per cubic centimeter, when placed in an electromagnetic field, will have eddy currents generated close to its surface. These eddy currents operate in the same manner as the eddy currents in a conductive shield surrounding a vacuum tube or the like, preventing penetration of the electromagnetic field below the region in which the eddy currents are generated. Typically in the case of the human body such eddy currents are generated in a more highly conductive subcutaneous layer lying slightly beneath the surface of the skin. Eddy currents are usually not generated in the skin surface because the surface cells of the skin are dead and of substantially less conductivity.

In accordance with the present invention, a radio frequency current is directly passed through the portion of the body in which the tumor is located by attaching uninsulated electrodes to the body to include it in an electrical circuit. By passing such a current through a malignant tumor and the surrounding tissue approximately uniformly, heating of the tumor and the surrounding tissue will occur due to heating proportional to the product of the tissue or tumor resistance and the square of the current passing therethrough. Because the circulation rate and hence the cooling effect in the tumor is substantially lower than that in the healthy surrounding tissue, the tumor heats to a higher temperature. Some observations have indicated that the higher temperature of the tumor may also result in a further decrease in circulation within the tumor, and it is estimated that temperature increase within the tumor can be as much as 2 to 3 times as great as in the surrounding tissue. By selecting a predetermined upper temperature limit for the surrounding tissue and/or the body as a whole, for example 104° F. as measured orally, the current may be regulated such that the surrounding tissue does not exceed the predetermined temperature but the temperature of the tumor being treated does exceed the predetermined temperature. Because the temperature of the tumor typically exceeds the predetermined temperature by a substantial magnitude, by maintaining this temperature differential for a sufficient period of time, the tumor may be killed.

Further, the treatment of tumors with a combination of heat and chemotherapy or heat and radiation has been extensively reported in the literature. (See Cancer Research, 30: 1632-1631, 1970, Effects of Elevated Temperatures and Drugs on the Viability of L1210 Leukemia Cells; or European J. Cancer, 8: 573-576, 1972, Investigations of II the Action of Combined Heat-Roentgen Treatment on a Transplanted Mouse Mammary Carcinoma). This invention may be used to heat tumors in conjunction with treatment by chemotherapy or Roentgen radiation in such a way as to enhance the effectiveness of these treatments.

As previously mentioned, electric heating has been used in the past in attempts to treat tumors. Such heating, however, has been utilized in such a way that the phenomenon of different circulation rates between tumors and healthy tissue has not been taken advantage of. The present invention enables utilization of electric current for the purpose of taking advantage of the aforementioned difference in circulation rates by efficiently coupling the electric energy to the tissue being treated while at the same time providing protection from low frequency transients which could cause physiological harm to the patient being treated.

Referring now more particularly to FIG. 1, apparatus for performing the method of the invention is illustrated. The apparatus includes a radio frequency oscillator 11 of any suitable type for providing a radio frequency output. For reasons which are explained below, this frequency should be less than about 40 MHz and greater than about 2 MHz. The Federal Communications Commission in the U.S.A. has allocated 13.56 MHz or the second or third multiple thereof as the frequencies to be used in diathermy equipment, and 13.56 MHz is preferred over the higher multiples.

The output of the oscillator 11 is coupled to a radio frequency amplifier 13. Both the oscillator and the amplifier are powered by a suitable power supply 15, and a feedback circuit 17 is provided from the amplifier to the oscillator as a stabilizing device. The amplifier is provided with two outputs indicated at 19 and 21. Both the outputs 21 and 19 are utilized together to provide an RF output therebetween.

As illustrated in FIG. 1, a radio frequency coaxial plug 23 is utilized to connect a coaxial cable 25 to the output 21 of the amplifier 13. Suitable ground connections 27 are provided to the sheath or shield of the cable 25 as is known in the art. The coaxial cable 25 is connected to a conductive uninsulated electrode shown in the form of a plate 31. Similarly, a radio frequency coaxial plug 22 is utilized to connect a coaxial cable 24 to the output 19 of the amplifier 13. Suitable ground connections 26 are provided to the shield of the cable 25 as is known in the art. The coaxial cable 24 connects the output from the terminal 22 of the amplifier 13 to a conductive uninsulated electrode shown in the form of a plate 32.

In addition, the sheaths of the cables 24 and 25 are interconnected by a flexible jumper cable 39, also coaxial. The cable 39 is connected by both central conductor and sheath to the sheaths of the cables 24 and 25 at the ends of the cables 24 and 25 just inside of the handles 33 and 34. The jumper lead 39 has the function of reducing the voltage drop between the open ends of the cable sheath, that is between the ends farthest from the power source. It also reduces the voltage drop between the power ground and the open ends of the sheath by providing a return path for the ground-side currents. The power coupling to the paddles or electrodes 31 and 32 is improved by a ratio of two to three times over the case where a jumper cable is not employed. The flexibility of the cable 39 allows freedom of positioning of the electrodes 31 and 32.

The electrodes 31 and 32 are of a shape suitable for the purpose of applying an electric field of the desired configuration. They may be in the form of plates, as shown, having a diameter about ten to twenty percent greater than the maximum dimension of the tumor in a plane perpendicular to the field. Shapes other than plates may also be utilized for better electrical contact, such as flexible or deformable conductive material. The thickness and shape of the electrodes 31 and 32, and the material thereof, are selected to provide good electrical conductivity and substantially uniform current distribution between their larger surfaces. Thus, a material having good electrical conductivity, such as gold, silver, copper or aluminum is used. In a typical application, the electrodes 31 and 32 are provided with insulating handles 33 and 34 to assist in manual placement of the electrodes 31 and 32.

A capacitance is built into the apparatus for the purpose of preventing low frequency transient voltage pulses from reaching the tissue being treated. When the radio frequency power source is turned on or off, frequencies are present in the circuitry, as may be shown by Fourier series analysis, which may extend down to d-c. In the illustrated apparatus, high voltage highly stable capacitors 28 and 29 are placed in series with the circuit formed by the electrodes and the tissue. The values of the capacitors 28 and 29 are selected to prevent very low frequencies and d-c from reaching the tissue. A typical value for each would be 200 pF, with a breakdown potential of 500 volts for safety. As illustrated, the capacitors 28 and 29 are in the handles 34 and 33, respectively. However, they may be placed elsewhere in the circuit, for example, within the amplifier 13, but provide the greatest safety when close to the electrodes, as in the handles. As a rough rule, the capacitors 28 and 29 may be selected to have a capacitive reactance approximately equal to the inductive reactance of the coaxial cables.

The inductance of the circuit formed by the amplifier, cables, electrodes and the tissue between the electrodes, is selected such that the resulting inductive reactance provided in the circuit approximately balances and cancels out the capacitive reactance of the circuit provided by the plates, thereby ensuring that good coupling of the electric field into the tissue will result. The inductance of the coaxial cables themselves may be sufficient, or series chokes, not shown, may be employed. By choosing an inductance in the circuit equal to the capacitance as determined by the capacitors 28 and 29 plus any other residual capacitance in the circuit, the capacitive reactance of the circuit is substantially equal to the inductive reactance (and 180° out of phase).

Because the electrodes 31 and 32 may be polished metal, rather than insulated, the possibility of the coated electrode developing scratches through which current could pass is avoided. The stable accurately known capacitance in the circuit does not vary in capacitance as compared with variations in the capacitance of any insulation coating on the electrodes as the coating varies in thickness and fabrication. Nevertheless, the patient is adequately protected from transients.

The tissue into which the electric field is being coupled, is indicated substantially in cross section at 36 which may represent, for example, a portion of a human body. A tumor may be located at 38. Where surface irregularities exist, such as the undulations illustrated, coupling may be assisted by using a conductive deformable material 37, such as copper "wool", between the electrodes 31 and 32 and the undulating surfaces 35. Thus, irregularities such as those produced by ribs and other bony structures or by a protruding tumor are easily accommodated. A further improvement in coupling results if the skin surface is coated with a conductive paste, such as the jelly used when attaching the electrodes of an electrocardiogram machine.

It is important that the conductive electrodes or paddles 31 and 32 can be connected to the skin or tissue surface with as good an electrical connection as possible. The copper wool or other deformable conductive material 37, as previously mentioned, takes up the irregularities and improves coupling from the electrodes into the tissue. A flexible electrode may be an alternative possibility or the use of a mesh of wires or a conductive coating on skin may also make it possible to conduct the current into the tissue. Higher voltages are required with poorer coupling in order to carry the current, and the current density will also be correspondingly higher with a consequent higher risk of damage to the skin or the healthy tissue. Moreover, with higher current densities and higher voltage levels, control over the power being applied to the tissue is more difficult.

The shape of the electrodes, as previously mentioned, may be circular, but other shapes are possible within the scope of the invention. The shape primarily depends upon the shape and location of the tumor being treated but in every case it is significant that the electric current density be as uniform as possible and that the tumor be fully included within the uniform portion of the electric current. To this end, the electrodes or paddles may be held in place by any suitable means such as by hand, by an external mechanical structure, by adhesive tape, or by a conductive adhesive on the surface of the tissue.

In many cases, it is desirable to cool the electrodes in order to insure that the patient's skin will not be damaged. To this end, a suitable coolant system, not shown, may be connected to passages, not shown, formed in the electrodes 28 and 29 for circulating a coolant, such as water, therein.

As previously mentioned, the frequency at which the apparatus operates should be less than about 40 MHz and greater than about 2 MHz. At frequencies greater than about 40 MHz, the electrodes or paddles, and some other structural items, begin to act as antennae and radiate in all directions. Above 40 MHz, this radiation becomes significant and results in a significant wasting of power and therefore a substantially less efficient apparatus. Moreover, above about 40 MHz frequency, the surface of the tissue has a tendency to heat undesirably. This can be dangerous, especially to eye tissue. Other undesirable effects of operation at relatively high frequencies is that losses in a coaxial cable increase with increasing frequencies and that heat dissipation internally of the RF oscillator or amplifier may present a problem. Naturally, considerations of allocation of frequencies by government agencies is also a significant factor. Further difficulty with relatively higher frequencies include increased cost of manufacturing the apparatus, difficulty in controlling and measuring the actual RF current going to the tissue, and a wandering of the electric current at higher frequencies.

More significant, however, from a practical standpoint is the limitation that frequency places upon the length of coaxial cables which may be employed. The longer the coaxial cable length is relative to the wavelength at the frequency used, the more sensitive the circuit becomes to variables such as the resistive and capacitive loads and the electrode configuration. This is because any shunt capacitive load at the end of a coaxial cable substantially increases its "electrical" length. Thus, a substantial increase in control problems results where the coaxial cable length is long relative to the wavelength at the particular frequency selected.

As a practical matter, it has been determined that the total length of the coaxial cables, including the length inside of the apparatus itself, should be well below about one-tenth of the electrical wavelength at the frequency being used. At the 13.56 MHz allocated for diathermy equipment, the wavelength is about 21.1 meters in free space. Since the velocity of the transmission in a coaxial cable is about 60-70% that of free space, the coaxial cable electrical equivalent of one wavelength is about 13.3 to 15.5 meters. With a length of coaxial cable inside the chassis of less than 20 centimeters and the leads to the probes being 70 centimeters, a total of 90 centimeters results-less than one sixteenth of a wavelength.

Naturally, the frequency used should also be above that of any neuromuscular reaction. A lower limit of about 2 MHz assures this. Experiments on simulated tissue at frequencies extending over the range of about 2 MHz to about 15 MHz indicate very little variation in heating efficiency between different frequencies in the range.

In applying the electric current to tissue in accordance with the invention, it is important to prevent excessive damage to the healthy tissue while at the same time maintaining a high enough temperature in the tumor over a sufficient period of time so as to kill the tumor. The fact that the maintenance of a high enough temperature over a sufficiently long period of time will kill many types of tumors is, as previously mentioned, documented in the prior art. Applicant's invention has provided a method and means for accomplishing this through the use of electric current wherein it is possible to closely control the amount of energy being applied to the tissue and thus closely regulate the temperatures in accordance with the desired treatment. The use of frequencies in the range previously specified, together with the avoidance of high loss factors, make it possible to employ electric current in such a way as to destroy tumors without significant damage to the surrounding healthy tissue. Using a heating rate of about 20 minutes for a 5° F. rise in the healthy tissue surrounding the tumor, the temperature inside a tumor has been observed to increase from two to three times as much as the temperature in the surrounding healthy tissue.

Referring now more particularly to FIG. 2, there is illustrated a schematic diagram of circuitry for use as the RF oscillator 11 and the amplifier 13. A 60 c.p.s. 117 V. or other suitable a-c supply is applied to the primary winding 43 of a power transformer 45, the primary being bypassed to ground through a capacitor 47. Included in the power transformer 45 is a secondary winding 49 to which are connected the filaments of the vacuum tubes described below. The secondary winding 51 of the power transformer 45 is connected across a diode bridge rectifier 53. Completing the diode circuitry are a pair of resistors 57 and 59 connected across opposite corners of the bridge, capacitors 61 and 63 in parallel therewith, respectively, and a capacitor 65 connected in parallel with the capacitors 61 and 63. The junction between the capacitors 57 and 59 is connected to the junction between the capacitors 61 and 63.

A center tap 67 on the secondary winding 51 is connected through a diode 69, a resistor 71, a filter capacitor 9 to ground, and resistors 73 and 75 to the screen of a tetrode 77. The resistors 73 and 75 are connected to ground through a capacitor 76. The tetrode 77 functions as the RF oscillator element in the oscillator 11, having its grid connected to a bias source terminal 79 through a resistor 87 and a tank circuit. The tank circuit includes a quartz crystal 81, a coil 83 and a resistor 85 in series with the coil 83. The plate of the tetrode 77 is connected to the choke 105 and through a plate capacitor 89, to the resistors 115, 117 and 119, in the control grids of tetrodes 109, 111 and 113. Coupled to the low side of the choke 91 is a capacitor 95 and a pair of series resistors 97 and 99 connected in parallel with the capacitor to ground. The cathode of the tetrode 77 is grounded through a capacitor 101 and parallel resistor 103. The bias source is from 79.

The RF output of the tetrode 77 at the plate thereof is coupled through a tuned circuit including a coil 105 and a variable capacitor or tuning capacitor 107 to a parallel amplifier including three tetrodes 109, 111 and 113. RF drive and grid bias for the three amplifier tubes is provided through resistors 115, 117 and 119, respectively. Plate voltage for the tetrode 109 is supplied through a choke coil 127 and the parallel combination of a resistor 129 and a coil 131 from the diode bridge rectifier 53. The parallel combination of the resistor 133 and coil 135 supplies the plate voltage for the tube 111 and the parallel combination of the resistor 137 and the coil 139 provides the plate voltage for the tube 113. The tubes 109, 111 and 113, therefore, operate in parallel to amplify the output of the RF oscillations of the tube 77.

The contacts 123 of a relay 125 are interposed between the resistor 121 and the plate of the tetrode 77. One side of the relay 125 is connected to ground through a normally closed reset switch 124. The other side of the relay 125 is connected through a resistor 126 to the cathode of the tube 77.

The amplified oscillations of the RF oscillator-amplifier 11 are developed across an output transformer having a primary winding 145 in series with the capacitor 147 and having a variable capacitor 149 connected thereacross. The smaller secondary winding 151 of the output transformer passes its signals through a shielded coaxial cable 153 having a tuning capacitor 155, through a coupling capacitor 157 to the amplifier 13.

The amplifier 13 includes a pair of parallel triodes 159 and 161. The grids of the triodes are grounded and the input from the RF oscillator 11 is coupled to the cathodes of the triodes 159 and 161 through the coupling capacitor 157. The plate output circuit of the triode 159 includes a parallel combination of a coil 165 and resistor 167. The plate output circuit of the triode 161 includes the parallel combination of a coil 169 and a resistor 171. The d-c voltage is provided from a high voltage terminal 175 through a choke coil 177 and a further choke coil 179. A capacitor 181 bypasses the coils 177 and 179 to ground.

A capacitor 172 couples the plate RF output of the parallel triode amplifiers 159 and 161 through an autotransformer 173. The autotransformer 173 includes a tap 183 which is grounded. A further winding on the transformer 173 has a tap 185 which is connected to a terminal 187. A tap 189 toward the higher voltage end of the transformer 173 is connected to a terminal 191. A further tap 193 closer to the input end of the transformer 173 than the tap 189 is connected to a terminal 195. The transformer 173 is tuned by a variable capacitor 197.

The output of the amplifier 13 is derived through a relay with one contact 201 for a left channel and a second contact 203 for a right channel. The relay contact 201 in the illustrated position connects to a terminal 187. The relay contact 203 connects with the terminal 191 thereby supplying a radio frequency signal between the tap 189 and ground. This signal is applied through a meter 207 to the output socket or terminal 21. The output from the terminal 187 is applied through a meter 209 to the left socket or output terminal 19.

For the purposes of stabilization, control, and to provide a low impedance generator source, a d-c coupled servo loop or feedback loop is provided. The servo loop includes a voltage doubler diode 211 in which the left-hand one of the plates is coupled through a pair of capacitors 213 and 215 to the terminal 195. A variable capacitor 217 is connected between that plate and its corresponding grounded cathode for adjusting the power level at which the apparatus is being operated. The right-hand plate of the diode 211 is connected through a resistor 219 and a diode 221 to the coil 83 of the grid return of the tetrode oscillator tube 77 in the oscillator-amplifier 11. The signal thus applied is developed across the parallel combination of the resistor 222 and capacitor 224 in the oscillator 11. The plate signal is developed across a capacitor 227 connecting the plate side of the resistor 219 to ground. A capacitor 225 connects the opposite side of the resistor 219 to ground. A capacitor 231 is connected to ground from the opposite side of the diode 221 from the resistor 219. The right-hand cathode of the doubler diode 211 is connected to the left-hand plate such that the dual diodes of the tube 211 are coupled in series. Adjustment of the capacitor 217 sets the power level at which the apparatus operates by adjusting the grid voltage of the tube 77, and is capable of an approximate fifteen-fold variation.

The above discussed circuit configuration permits the apparatus to be operated by a single control adjusting the capacitor 217. There is no need for, nor can the operator of the apparatus to do any tuning of the circuit. This is because the direct current inverse feedback provided by the circuit 17 stabilizes the current at any given control setting even if the resistive and/or capacitive loads vary.

In the event that the doubler diode 211 fails, power output may tend to increase dangerously. To prevent this, the relay 125 is set to open the contacts 123 when the cathode current of the tube 77 increases beyond a preselected level. When the relay switch or contacts 123 open, screen bias to the tubes 109, 111 and 113 is removed, cutting off the RF power.

In practicing the method of the invention, after the electrode or electrodes are positioned with respect to the patient, the power is turned on. Temperature is continuously monitored, preferably in the healthy tissue near the tumor and in the tumor itself. Since this may be impractical, the patient's rectal and/or oral temperature alone may be monitored. In addition, the skin temperature within the field should also be monitored. Since the body acts as a heat sink which is relatively large compared with the volume of healthy tissue which is heated by the field, the healthy tissue near the tumor is typically very close to the oral or rectal temperature. On the other hand, because of relatively poorer vascularization, the tumor may be expected to rise to a substantially higher temperature.

The current input to the patient is controlled so that the tumor heats to a lethal temperature while the temperature of the healthy tissue does not rise above 41.5° C., preferably 41° C. or less. The lethal temperature, of course, varies in accordance with the type of tumor, its size, or sometimes its location. The lethal temperature also is related to the duration of the treatment. Some tumors with low heat resistance may be killed at a temperature of 43° C. in as short a time as twenty minutes. On the other hand, old, heat-resistant tumors of certain types may require as high a temperature as 47° C. for as long as forty minutes or longer. By killing the tumor, it is meant that a condition is achieved wherein at least a substantial part of the tumor becomes necrotic within twelve hours. The time taken to achieve the desired temperatures is preferably at least about ten minutes to avoid shock to the patient and to allow the vascularization of the healthy tissue to improve. Ideally, the heating rate of the healthy tissue should be about one-half degree Centrigrade per minute.

Once the desired temperature is achieved, the current input is adjusted, if necessary, to maintain a substantially constant temperature level in the healthy tissue for at least about twenty minutes and not more than about forty minutes. Too short a heating period does not allow the tumor to rise to a sufficient temperature for a long enough time to do any significant damage. Too long a heating period may cause excessive damage to healthy tissue in contact with the tumor or have other undesirable side effects.

In occasional cases, the treatment is given on successive occasions. It may also be beneficial if the orientation of the current path is different for each treatment to ensure no part of the tumor is getting insufficient heat. For very large tumors, however, it is usually better to treat only a portion at a time, since complete destruction of the tumor all at once may be too much for the body to accommodate. However, it has generally been possible to remove "dead tissue" by carefully inserting an hypodermic needle into the treated tumor "and reduce the load" upon the normal removal processes of the body.

The region through which the electric current is passed is selected to completely encompass the tumor and extend, preferably, about ten to twenty percent of the tumor's transverse dimension on either side of it. The electrodes should be close to parallel with each other to maintain uniformity of the current distribution. In some situations, however, it may be useful to shape or position the electrodes to concentrate the current in one or more regions.

From experience with deep tumors in human patients, the current range from small (less than 2 centimeters cross-sectional long dimension) to large (such as 10 centimeters cross-sectional long dimension) will range from 0.4 to 2 amperes, the limit being set by the maximum rectal temperature.

After treatment, the tumor is allowed to remain in-situ. If the treatment has been successful, the tumor typically softens, sometimes even liquifies, and is absorbed by the body. Biopsies have indicated the material is comprised of dead cells and no danger exists of metastasis. In fact, some evidence indicates the body may produce an immune response and that distant metastases may regress or even disappear.

For the purpose of illustrating the apparatus of the invention, the following examples are given. It is not intended, however, that the invention be limited in any way to the specific parameters or procedures set forth in the examples.

EXAMPLE 1

To demonstrate the uniformity of heating and absence of skin eddy currents, apparatus constructed in accordance with the invention was utilized to pass an electric current through a bag containing three liters of salt-agar jelly. Using a radio frequency of 13.56 MHz, power levels of 300 to 400 watts were used. Temperatures were measured adjacent to opposite sides of the jelly and in the center of the jelly using highly accurately centigrade thermometers. With an increase in temperature of over 30° C. the maximum observed difference in temperature readings was 6.5° C. Where conditions and the configuration of the apparatus were carefully controlled, temperatures were maintained within 2° and in most cases substantially less. More importantly, however, there was no indication of a tendency for greater heating near the surface than in the center demonstrating that the degree of heating was uniform regardless of depth and was not affected by the presence of eddy currents in the skin as is the case typically in connection with electromagnetic fields.

EXAMPLE 2

Intramuscular VX2 carcinomas in the hind limb of seven rabbits were heat-treated utilizing the above described apparatus.

The VX2 tumor is a highly malignant, anaplastic squamous cell carcinoma that developed as a result of malignant change in the cells of a Shope virus induced skin papilloma in a domestic rabbit. The carcinoma in each of the seven rabbits treated was transferred, by serial inoculation of one million cells 1 cm. deep into the thigh muscle of New Zealand white rabbits weighing 2.0 to 2.5 Kg. The cells gave rise to a palpable tumor three weeks after injection. Untreated rabbits died within a further seven weeks (mean survival time 72±7 days) with metastases in the regional, iliac and para-aortic lymph nodes and in the lungs.

The intravascular VX2 tumors in the seven rabbits were heat-treated three to four weeks after incubation at temperatures of 47° C. for 30 minutes using less than 10 watts power. The 47° temperature was achieved gradually over a ten minute period. Temperature patterns within large tumors (15–22 ml) indicated less homogeneous heating than in smaller tumors. At 47° C. a temperature differential of 2°–3° C. was observed between multiple temperature sensors in the large tumors. Skin temperatures over the tumor remained at 43°–44° C. throughout the 30 minute heating period. The temperature of normal muscle situated 1 cm outside the area affected by the imposition of the RF power did not rise above 40° C. and the rabbits' rectal temperature remained within the normal range. Tumor and skin temperatures rapidly returned to normal when the RF power was turned off.

The seven VX2 carcinomas which were heat-treated with RF power at temperatures set forth above all regressed completely in six to eight weeks to result with cure of the host without damage to normal tissues.

It may be seen, therefore, that the invention provides an effective apparatus for treating tumors by causing the tumors to increase in temperature substantially above that of the surrounding healthy tissue. It is believed that such procedure causes the tumor to be destroyed in many cases, and that the resulting rise in temperature is due to the substantially reduced circulation present in malignant tumors. The invention is also capable of heating other types of tissue which have a substantially lower circulation rate than surrounding tissue to temperature higher than the surrounding tissue.

Various modifications of the invention in addition to those shown and described herein will become apparent to those skilled in the art from the foregoing description and accompanying drawings. Such modifications are intended to fall within the scope of the appended claims.

What is claimed is:

1. Apparatus for treating tumors in humans and animals, comprising, radio frequency oscillator means, amplifier means coupled to the output of said radio frequency oscillator means for producing an amplified radio frequency output signal, electrode means coupled to said amplifier means, said electrode means including a pair of uninsulated conductive electrodes having a configuration adapted to pass an electric current directly into the tissue to which they are attached for passing current through both the tumor and the surrounding tissue, said electrode means and said amplifier means forming with the tissue between said electrode means an electrical circuit, said electrical circuit exclusive of the tissue including inductance means and capacitance means selected such that the capacitive reactance of said circuit is substantially equal and opposite in phase to the inductive reactance thereof, the value of said capacitance means also being selected to prevent transient very low frequency pulses and direct current pulses occurring in said circuit when said amplifier means are turned on and off from reaching the tissue, and means for controlling the power of said amplifier means to avoid heating the surrounding tissue beyond a preselected temperature level while allowing the tumor to heat beyond the preselected temperature level.

2. The apparatus of claim 1 wherein said inductance means include coaxial cable means coupling said electrode means to said amplifier means, and wherein the capacitive reactance of said capacitance means is approximately equal to the inductive reactance of said coaxial cable means.

3. The apparatus of claim 1 wherein said electrode means include handle means, and wherein said capacitance means include at least one capacitor in said handle means.

* * * * *